(12) United States Patent
Finn-Henry et al.

(10) Patent No.: US 12,691,265 B2
(45) Date of Patent: Jul. 28, 2026

(54) ENDOVASCULAR SHUNTS AND METHODS OF SHUNTING

(71) Applicant: EndoShunt Medical, Inc., Chicago, IL (US)

(72) Inventors: Michael Finn-Henry, Lincoln, MA (US); Olivia Busk, Fairfield, CT (US)

(73) Assignee: EndoShunt Medical, Inc., Chicago, IL (US)

( * ) Notice: Subject to any disclaimer, the term of this patent is extended or adjusted under 35 U.S.C. 154(b) by 643 days.

(21) Appl. No.: 17/656,390

(22) Filed: Mar. 24, 2022

(65) Prior Publication Data
US 2022/0305241 A1 Sep. 29, 2022

Related U.S. Application Data

(60) Provisional application No. 63/166,133, filed on Mar. 25, 2021.

(51) Int. Cl.
*A61M 27/00* (2006.01)
*A61F 2/966* (2013.01)

(52) U.S. Cl.
CPC ........... *A61M 27/002* (2013.01); *A61F 2/966* (2013.01); *A61M 2210/12* (2013.01)

(58) Field of Classification Search
CPC .... A61F 2002/9511; A61F 2/844; A61F 2/86; A61F 2/82; A61F 2/07; A61F 2/962; A61F 2002/823; A61F 2002/072; A61F 2/966; A61F 2/852; A61F 2002/9623; A61F 2/9661; A61M 27/002; A61M 2210/12
See application file for complete search history.

(56) References Cited

U.S. PATENT DOCUMENTS

| | | | | |
|---|---|---|---|---|
| 5,876,445 | A * | 3/1999 | Andersen | A61L 31/04 623/23.7 |
| 5,957,974 | A * | 9/1999 | Thompson | A61F 2/07 623/1.53 |
| 6,176,875 | B1 * | 1/2001 | Lenker | A61F 2/90 623/1.49 |
| 7,004,926 | B2 * | 2/2006 | Navia | A61M 1/3613 604/4.01 |
| 9,060,777 | B1 * | 6/2015 | Wallace | A61F 2/07 |
| 9,724,215 | B2 * | 8/2017 | Tippett | A61F 2/91 |
| 9,925,074 | B2 * | 3/2018 | Hyodoh | A61F 2/0105 |
| 10,149,962 | B2 * | 12/2018 | Franklin | A61B 17/12036 |
| 10,758,386 | B2 * | 9/2020 | MacTaggart | A61B 5/02042 |
| 2001/0025195 | A1 * | 9/2001 | Shaolian | A61F 2/9661 623/1.13 |
| 2002/0165576 | A1 | 11/2002 | Boyle et al. | |
| 2004/0015224 | A1 * | 1/2004 | Armstrong | A61F 2/97 623/1.12 |

(Continued)

FOREIGN PATENT DOCUMENTS

WO 2006/119144 A1 11/2006

*Primary Examiner* — Adam Marcetich
*Assistant Examiner* — Ted Yang

(57) ABSTRACT

Endovascular assemblies may include a catheter, a shunt, and a wire. The shunt includes a frame and a liner secured about the frame. The wire extends through the catheter and is coupled to the shunt. The shunt is configured to move between a collapsed configuration and a radially expanded configuration in response to movement of the wire. Endovascular assemblies may be used to shunt a vessel.

34 Claims, 6 Drawing Sheets

(56)　　　　　References Cited

U.S. PATENT DOCUMENTS

| | | | | |
|---|---|---|---|---|
| 2006/0142836 | A1* | 6/2006 | Hartley | A61F 2/95 |
| | | | | 623/1.11 |
| 2006/0259119 | A1* | 11/2006 | Rucker | A61F 2/95 |
| | | | | 623/1.11 |
| 2011/0054594 | A1* | 3/2011 | Mayberry | A61F 2/856 |
| | | | | 29/446 |
| 2014/0343585 | A1* | 11/2014 | Ferrera | A61F 2/90 |
| | | | | 606/159 |
| 2014/0350694 | A1* | 11/2014 | Behan | A61F 2/966 |
| | | | | 623/23.65 |
| 2015/0190221 | A1* | 7/2015 | Schaefer | A61F 2/915 |
| | | | | 623/1.11 |
| 2016/0310303 | A1* | 10/2016 | Thapliyal | A61F 2/90 |
| 2017/0020542 | A1* | 1/2017 | Martin | A61F 2/88 |
| 2017/0071722 | A1* | 3/2017 | Rafiee | A61B 17/11 |
| 2017/0265869 | A1* | 9/2017 | Cibulski | A61B 17/12118 |
| 2017/0319215 | A1* | 11/2017 | Zanatta | A61B 17/12113 |
| 2019/0374228 | A1* | 12/2019 | Wallace | A61B 17/1214 |
| 2020/0163750 | A1 | 5/2020 | Ehnes | |
| 2021/0154031 | A1* | 5/2021 | Cerchiari | A61F 2/962 |
| 2021/0259839 | A1* | 8/2021 | Cole | A61B 17/11 |
| 2021/0315578 | A1* | 10/2021 | Khosrovaninejad | |
| | | | | A61B 17/1155 |
| 2022/0218352 | A1* | 7/2022 | O'Halloran | A61B 5/686 |

* cited by examiner

100

100

100

ENDOVASCULAR SHUNTS AND METHODS OF SHUNTING

CROSS-REFERENCE TO RELATED APPLICATIONS

This application claims the benefit of U.S. Provisional Application No. 63/166,133 filed Mar. 25, 2021, which is incorporated herein in its entirety by reference.

TECHNICAL FIELD

The present disclosure relates generally to endovascular devices, and more particularly to endovascular shunts and methods of shunting.

BACKGROUND

Hemorrhaging, and in particular those resulting in rapid blood loss, is a leading cause of preventable death. The vascular injuries resulting in such rapid blood loss are often reparable, but clinicians generally lack the means to control this blood loss prior to and while operating.

Surgical repairs of traumatic vascular injuries must be swift because of the often excessive rate of blood loss associated with injuries of this nature. During these surgical repairs, clinicians must control the rate of blood loss so that the patient remains stable and does not suffer a sudden decrease in blood pressure. Currently, clinicians have limited options for stabilizing hemorrhaging patients, including balloon occlusion.

When a patient's blood loss is so severe that their blood pressure is dangerously low, clinicians will often deploy an endovascular balloon to occlude the aorta, or surgically place a clamp across the aorta. Doing so cuts off blood flow to the patient's entire lower body, thereby directing critical blood and oxygen flow to their heart and brain. Because this measure is so extreme, it is classified is resuscitative and is only implemented in grave circumstances. Moreover, because blood flow to the body below the heart is suspended, there is a significant risk of permanent damage to the patient's abdominal organs from the ischemia if the surgical repair takes more than ten to thirty minutes.

Thus, there remains a need for endovascular shunts and methods of shunting, for example, capable of rapidly providing temporary targeted hemorrhage control.

SUMMARY

The present disclosure provides endovascular assemblies including shunts, and methods of shunting.

In some embodiments, an endovascular assembly includes a catheter, a shunt, and a wire. The catheter defines a transport lumen extending from a proximal end of the catheter to a distal end of the catheter. The shunt includes a frame and a liner secured about the frame. The wire extends through the transport lumen of the catheter and is coupled to the shunt. The shunt is configured to move, in response to a relative movement between the catheter and the shunt, between (1) a collapsed configuration within the transport lumen of the catheter and (2) an expanded configuration defining an expanded shunt lumen outside the transport lumen.

In some embodiments, an endovascular shunt includes a frame and a liner secured about the frame. The shunt is configured to move between (1) a collapsed configuration and (2) an expanded configuration defining an expanded shunt lumen.

In some embodiments, a method of shunting a blood vessel includes navigating an endovascular assembly including a catheter and a shunt within the catheter to a predetermined location within the blood vessel. The shunt includes a frame and a liner. The method further includes retracting a distal end of the catheter to cause the shunt to emerge from the catheter. The method further includes allowing the shunt to radially expand to define an expanded shunt lumen along the blood vessel. The method further includes allowing flow through the expanded shunt lumen along the blood vessel.

BRIEF DESCRIPTION OF THE DRAWINGS

The detailed description is set forth with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale.

DETAILED DESCRIPTION

The present disclosure relates generally to endovascular devices, and more particularly to endovascular shunts and methods of shunting.

Clinicians may employ a permanent or retrievable stent to control a patient's blood loss. However, both permanent and retrievable stents are placed during lengthy surgical procedures, and may not adequately mitigate rapid blood loss associated with traumatic vascular injuries. Further, there may be long term complications associated with permanent stents. While retrievable stents do not have the same complications associated with permanent stents, the removal procedure is long and complex.

The present disclosure describes rapidly deployable and removable endovascular assemblies that may be used to establish shunts in vessels. In some embodiments, endovascular assemblies according to the present disclosure may be advantageously deployable in relatively short periods of time, for example, 30 to 60 seconds. In some embodiments, endovascular assemblies according to the present disclosure may enable clinicians to temporarily control rapid blood loss while still allowing blood flow through the damaged vessel to the rest of the patient's body. Because the shunt controls hemorrhaging while maintaining blood flow, clinicians may be provided with sufficient time to surgically repair vascular damage.

In some embodiments, an endovascular assembly includes a catheter, a shunt, and a wire. The catheter defines a transport lumen extending from a proximal end of the catheter to a distal end of the catheter. The shunt includes a frame and a liner secured about the frame. The wire extends through the transport lumen of the catheter and is coupled to the shunt. The shunt is configured to move or transition, in response to a relative movement between the catheter and the shunt, between (1) a collapsed configuration within the transport lumen of the catheter and (2) an expanded configuration defining an expanded shunt lumen outside the transport lumen.

In some embodiments, an endovascular shunt includes a frame and a liner secured about the frame. The shunt is configured to move or transition between (1) a collapsed configuration and (2) an expanded configuration defining an expanded shunt lumen.

In some embodiments, a method of shunting a blood vessel includes navigating a shunt assembly including a catheter and a shunt within the catheter to a predetermined location within the blood vessel. The shunt includes a frame and a liner. The method further includes retracting a distal end of the catheter to cause the shunt to emerge from the catheter. The method further includes allowing the shunt to radially expand to define an expanded shunt lumen along the blood vessel. The method further includes allowing flow through the expanded shunt lumen along the blood vessel.

Figures 1A, 1B, 1D:
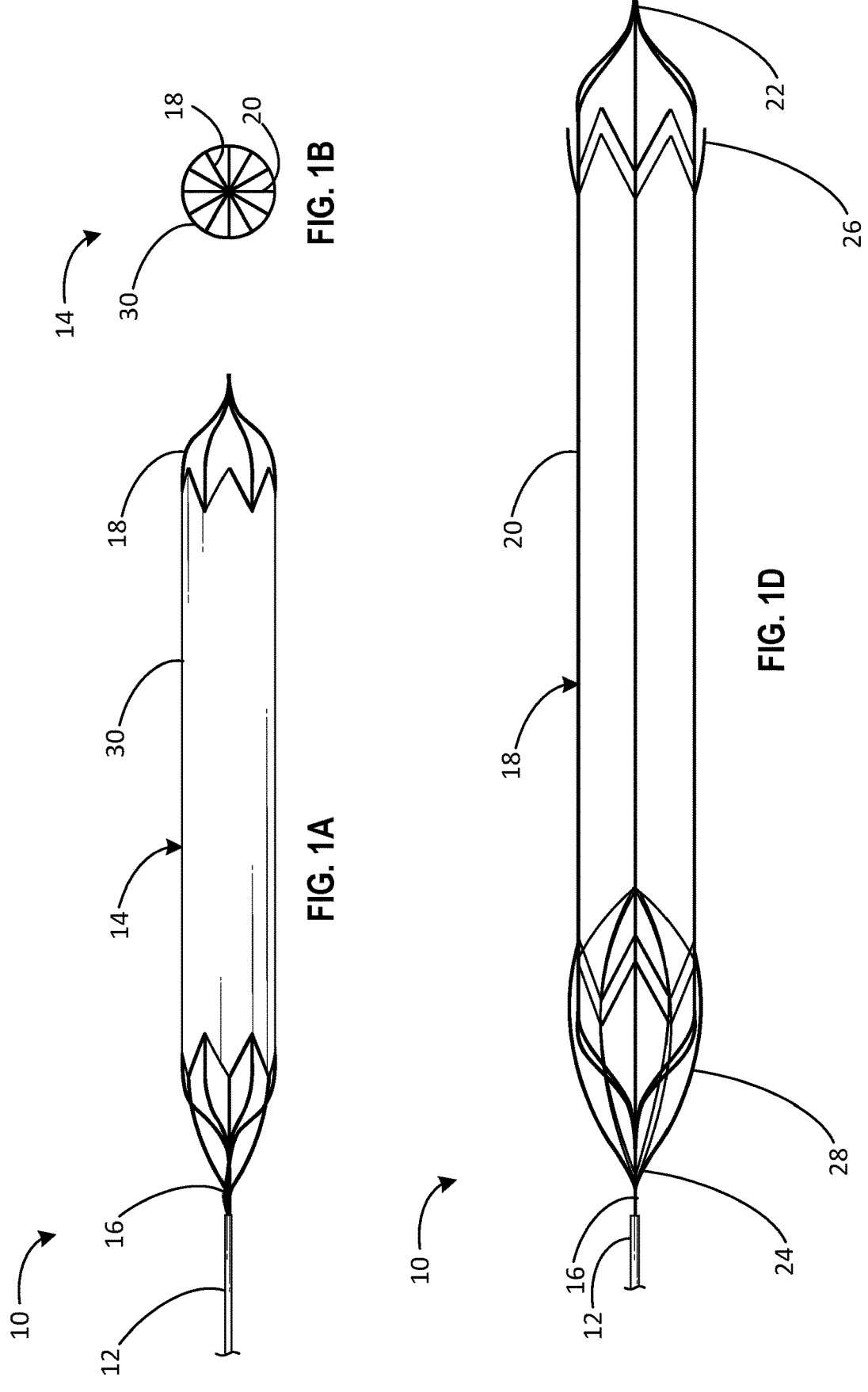
FIG. 1A is a partial side view of an endovascular assembly including a catheter, a shunt, and a wire.
FIG. 1B is a front view of the shunt of the endovascular assembly of FIG. 1A.
FIG. 1D is a side view of a frame of the shunt of FIG. 1B.
Figures 1C, 2A, 2B:
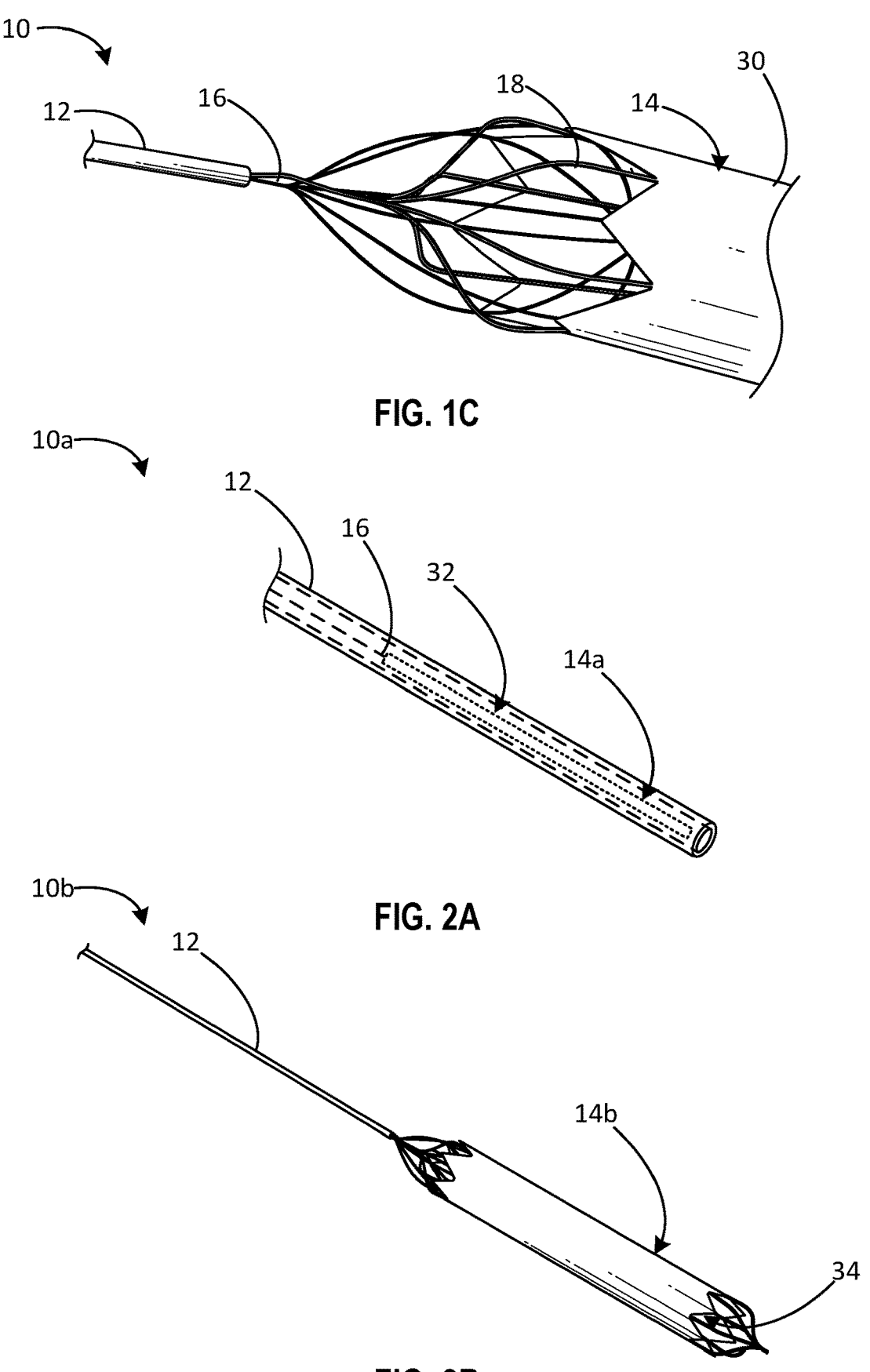
FIG. 1C is a partial perspective view of a proximal end of the endovascular assembly of FIG. 1A.
FIG. 2A is a partial perspective view of the endovascular assembly of FIG. 1A with the shunt in a collapsed configuration within the catheter.
FIG. 2B is a partial perspective view of the endovascular assembly of FIG. 1A with the shunt in an expanded configuration.

FIG. 1A is a side view of an endovascular assembly 10 including a catheter 12, a shunt 14, and a wire 16. FIG. 1B is a front view of the shunt 14 of the endovascular assembly 10 of FIG. 1A. FIG. 1C is a partial perspective view of a proximal end of the endovascular assembly 10 of FIG. 1A. The catheter 12 defines a transport lumen (not shown in FIGS. 1A to 1D) extending from a proximal end of the catheter 12 to a distal end of the catheter 12. The catheter 12 may have any suitable diameter and length. In some embodiments, the catheter 12 is a 1 meter long Pebax® French size 7 catheter.

The shunt 14 is configured to move, in response to a relative movement between the catheter 12 and the shunt 14, between (1) a collapsed configuration within the transport lumen of the catheter 12 and (2) an expanded configuration defining an expanded shunt lumen outside the transport lumen. In some embodiments, the shunt 14 is configured to transition between the collapsed configuration and the expanded configuration in response to a relative movement between the catheter 12 and the wire 16, or between the shunt 14 and the wire 16.

The wire 16 extends through the transport lumen of the catheter 12 and is coupled to the shunt 14. In some embodiments, the wire 16 may extend along an exterior of the catheter 12, or otherwise outside catheter 12. The wire 16 may be moved to cause the shunt 14 to shorten or elongate in length, as described elsewhere in the disclosure. The wire 16 may also be used to hold or move the shunt 14 in a particular position relative to the catheter 12. The wire 16 may include a metal, an alloy, or a polymer. The wire 16 may be coated with a coating, for example, a lubricious coating, or a biocompatible coating, as known in the art. The wire 16 may remain coupled to the shunt 14 throughout the time the shunt is transported, deployed, used, and withdrawn. Keeping the wire 16 coupled to the shunt 14 may avoid a need for reengaging or recoupling the wire 16 to the shunt 14, or otherwise to use a retrieval mechanism to remove the shunt 14 after use.

FIG. 1D is a side view of a frame 18 of the shunt 14 of FIG. 1A. The frame 18 may include any suitable rigid material, or a relatively stiff and elastic material, capable of substantially maintaining a form or a shape. In some embodiments, the frame 18 includes a metal, an alloy, a polymer, or any combination thereof. In some embodiments, the frame includes nitinol. In a particular embodiment, the frame 18 consists of, or consists essentially of, nitinol. The shunt 14 may include a single frame 18, or more than one frame. The frame 18 may be formed as a single unitary or integral piece, or include multiple distinct pieces.

In some embodiments, the frame 18 is biased to expand radially. For example, in the absence of a constraining force, the frame 18 will tend to expend outward or radially. The frame 18 may alternatively expand in response to a movement of the wire 16 relative to the shunt 14, to the frame 18, or to the catheter 12. For example, the frame 18 may not be biased to expand, and may expand in response to an external force. The frame 18 may expand to a predetermined extent, for example, to a predetermined maximum diameter or a predetermined maximum transverse dimension. The radial expansion may cause the shunt 14 to expand from a collapsed configuration to an expanded configuration when the shunt 14 emerges from the distal end of the catheter 12. The frame 18 may be configured to radially collapse, for example, when a radially inward constraining force is applied.

Frame 18 may be configured to collapse when a proximal end of the shunt 14 is withdrawn proximally into the distal end of the catheter 12. For example, a catheter wall may engage with and exert a progressive radially inward force as the shunt 14 is withdrawn into the catheter 12 (or alternatively, as the catheter 12 is advanced relative to and over the shunt 14). The frame 18 may thus be configured to move between a collapsed configuration and an expanded configuration, which in turn may cause the shunt 14 to move between a collapsed configuration and an expanded configuration.

In some embodiments, the frame 18 includes a plurality of rails 20. The plurality of rails 20 may be radially disposed about a center point of the shunt 14, as shown in FIG. 1B. For example, the plurality of rails 20 may be symmetrically or asymmetrically disposed about the center of the shunt 14. The rails 20 may taper and join together at a distal end 22 of the frame 18. Similarly, the rails 20 may also taper and join together at a proximal end 24 of the shunt 14. In some embodiments, the distal end 22 or the proximal end 24 point may be connected to the wire 16.

The rails 20 may be biased to apply an outward radial force about the shunt 14 to maintain an inner diameter of the shunt 14 when the shunt 14 is unconstrained. The rails 20 may also be configured to collapse when a radially inward force is applied to the shunt 14, for example, by moving radially inward to reduce a transverse diameter of the shunt 14.

The frame 18 may include one or both of a distal anchor 26 or a proximal anchor 28. One or both of the distal or proximal anchors 26 or 28 may be free to move along the frame 18, for example, along the rails 20. In some embodiments, the distal anchor 26 is fixedly secured to the frame 18, while the proximal anchor 28 is movably secured to the frame 18, for example, along the rails 20.

One or both of the distal or proximal anchors 26 or 28 may be circular or spherical, with rounded or pointed ends. For example, the distal or proximal anchors 26 or 28 may resemble the shape of an ellipsoid or a football.

In addition to, or instead of, the rails, the frame 18 may include struts in a predetermined pattern. The pattern of struts may accommodate dimensional changes that allow the frame 18 to collapse and expand radially. In some embodiments, the frame 18 includes a laser cut pattern.

The shunt 14 includes the frame 18 and a liner 30 partially or entirely secured about the frame. The liner 30 may include a fabric or a film. The fabric or the film may be formed of any suitable material, such as a natural or artificial material known in the art. The material may include a polymer. For example, the liner 30 may include a flexible polymer. In some embodiments, the material may be semi-permeable. In some particular embodiments, the liner 30 consists of, or consists essentially of, the flexible polymer. The polymer may include polytetrafluoroethylene (PTFE), silicone, latex, thermoplastic polyurethanes, or other suitable biocompatible polymers. The liner 30 may provide a fluid barrier about the shunt 14, and reduce or prevent transverse or radial flow of fluid across the shunt 14, while substantially permitting flow along a length of the shunt 14.

The entire liner 30 or a portion thereof expands when the frame 18 expands, and collapses when the frame 18 collapses. In some embodiments, the liner 30 may fold in certain regions when the frame 18 collapses. In some embodiments, the liner 30 may flexibly exhibit a reduction in surface area when the frame 18 collapses, without folding. The liner 30 may attach around the rails 20 so that the liner 30 may slide along the rails 20 without detaching from the rails 20, ultimately, from the frame 18. In some embodiments, one or both of the distal or proximal anchors 26 or 28 may attach to the liner 30 in some manner. In some particular embodiments, the liner 30 is substantially free between the proximal anchor 28 and the distal anchor 26. The liner 30 may be secured about a portion of the frame 18.

The proximal anchor 28, shown in greater detail in FIGS. 1C and 1D, may be positioned at the proximal end of the shunt 14 and may attach to the interior surface of the liner 30 such that at least a portion of the proximal anchor 28 is disposed within the shunt 14. In some embodiments, the proximal anchor 28 may be disposed entirely outside of the shunt 14, and the liner 30 may be affixed to the interior of the proximal anchor 28, to allow it to more smoothly enter the catheter 12.

FIG. 2A is a partial perspective view of a collapsed configuration 10a of the endovascular assembly 10 of FIG. 1A with the shunt 14 in a collapsed configuration 14a within the catheter 12. FIG. 2B is a partial perspective view of an expanded configuration 10b of the endovascular assembly 10 of FIG. 1A with the shunt 14 in an expanded configuration 14b. The shunt 14 is configured to move, in response to a relative movement between the catheter 12 and the shunt 14 or the wire 16, between (1) the collapsed configuration 14a within a transport lumen 32 of the catheter 12 and (2) the expanded configuration 14b defining an expanded shunt lumen 34 outside the transport lumen 32.

The shunt 14 may move between the collapsed configuration 14a and the expanded configuration 14b in response to relative motion between the catheter 12 and the shunt 14 or in response to relative motion between the catheter 12 and the wire 16. When the shunt 14 is in the collapsed configuration 14a, as shown in FIG. 2A, the shunt 14 may be disposed within the transport lumen 32 of the catheter 12. With the shunt 14 in the collapsed configuration 14a, the endovascular assembly 10 may be transported through a patient's vasculature to the site of the patient's vascular injury.

To deploy the shunt 14 into the expanded configuration 14b, which is shown in FIG. 2B, the catheter 12 may be retracted relative to the shunt 14. As the catheter 12 is retracted, the shunt 14 may emerge from the transport lumen 32, for example, from a distal end or opening of the catheter 12. The shunt 14, or the frame 18, may be biased to radially expand when deployed from the transport lumen 32 of the catheter 12. The radial expansion may be to a suitable predetermined maximum diameter, for example, 1 cm, 2 cm, or 3 cm. It may be understood that the shunt 14 may not always expand to the maximum diameter, depending on obstructions or constraints adjacent the shunt 14.

The shunt 14 may be returned to the collapsed configuration 14a from the deployed or expanded configuration 14b by advancing the catheter 12 over the shunt 14 (or by withdrawing the shunt 14 into the catheter 12). As the catheter 12 is advanced (or the shunt 14 withdrawn), the frame 18 and the liner 30 may collapse so that the shunt 14 may fit within the transport lumen 32 of the catheter 12. When the shunt 14 is fully contained within the transport lumen 32 in the collapsed configuration 14a, the catheter 12 may be removed from a patient's vasculature.

The shunt 14 may be deployed blindly (e.g., without the aid of imaging or a guidewire) to relatively rapidly provide a shunt in a vessel of a patient, for example, allowing immediate control of the patient's blood loss. Positioning of the shunt 14 may therefore need to be adjusted as the clinician gathers additional information about the patient's injuries. For example, a patient with a traumatic vascular injury will likely have a very low and/or rapidly decreasing blood pressure. In such instances, a clinician may prefer to mitigate blood loss as quickly as possible to stabilize the patient's vital signs. The clinician will fully assess the extent of the injury once the patient is stable, and in some cases a need may arise to adjust the position and/or length of the shunt 14.

In addition to controlling the diameter (collapsed and expanded), the frame 18 may enable a clinician to adjust the position and/or the length of the shunt 14 after it has been deployed within a patient's vasculature. For example, the position of the endovascular assembly 10 may be adjusted in either the collapsed configuration 10a or the expanded configuration 10b. In the collapsed configuration 10a, the position of the endovascular assembly 10 may be adjusted by navigating the catheter 12 to different position within a patient's vasculature. In the expanded configuration 10b, the entire endovascular assembly 10 may be moved forward or backward so that the shunt 14 is similarly moved. In moving the endovascular assembly 10, the relative position of the shunt 14 with respect to catheter 12 may remain unchanged. The relative position of the proximal anchor 28 with respect to the distal anchor 26 may also remain unchanged.

The length of the shunt 14 may be controlled by a motion of either the proximal anchor 26 or the distal anchor 28 relative to each other, or to the shunt 14, or to the catheter 12. In some embodiments, the frame 18 is configured to move along a direction along the shunt 14 between an elongated configuration and a shortened configuration in response to a relative movement between the wire 16 and the catheter 12. In some embodiments, the radial dimension of the shunt 14 is substantially unchanged in the elongated configuration and the shortened configuration. In some embodiments, the wire 16 is coupled to a distal end 22 of the frame 18. In some other embodiments, the wire 16 is coupled to the proximal end 24 of the frame 18.

The endovascular assembly may include more than one wire. For example, the wire 16 may be a proximal wire coupled to the proximal end 24 of the frame 18, and the endovascular assembly 18 may further include a distal wire coupled to the distal end 22 of the frame 18. In some such embodiments, the frame 18 is configured to change in length in response to a relative movement between the proximal wire and the distal wire.

In some embodiments, the distal wire may be coupled to the distal anchor 26, and/or the proximal wire may be coupled to the proximal anchor 28. Movement of the distal anchor 26 and/or of the proximal anchor 28 may respectively be controlled by the distal wire or the proximal wire.

The wire 16 (or any additional wires) may be disposed within the transport lumen 32 and span at least the entire length of the catheter 12. One or more of the wires may also be contained within a cannula or a sheath (not shown in FIGS. 1A to 2B) to maintain the collinearity of the wires. This cannula or sheath also may be disposed within the transport lumen 32 of the catheter 12.

In some embodiments, the proximal anchor 28 is movable relative to the distal anchor 26. To move the proximal anchor 28, the proximal wire may pushed towards the distal end 22 of the shunt 14. As the proximal anchor 28 advances towards the distal end 22 of the shunt 14, the liner 30 may be longitudinally compressed or shortened, thereby decreasing the overall length of the shunt 14.

In some embodiments, the distal anchor 26 is movable relative to the proximal anchor 28. To move the distal anchor 26, the wire 16 may be attached to the distal anchor and pulled towards the proximal end of the shunt 14. The proximal anchor 28 may maintain the proximal end 24 of the shunt 14 in a fixed position despite the movement of the distal anchor 26. As the distal anchor 26 advances towards the proximal end 24 of the shunt 14, the liner 30 may be compressed or shortened, thereby decreasing in length.

The distal tip 22 and rails 20 may begin to collapse and/or enter the transport lumen 32 of the catheter 12 as the wire 16 is pulled in the proximal direction. It is therefore possible that the overall the length of the shunt 14 may decrease as the length of the liner 30 decreases.

In this way, the shunt 14 may be movable between radially collapsed and expanded configurations, and/or longitudinally shortened and elongated configurations.

While the frame 18 of FIGS. 1A to 2B may include the rails 20, other frames according to the present disclosure may have a different structural configuration that permits dimensional changes.

Figures 3A, 3B, 3C:
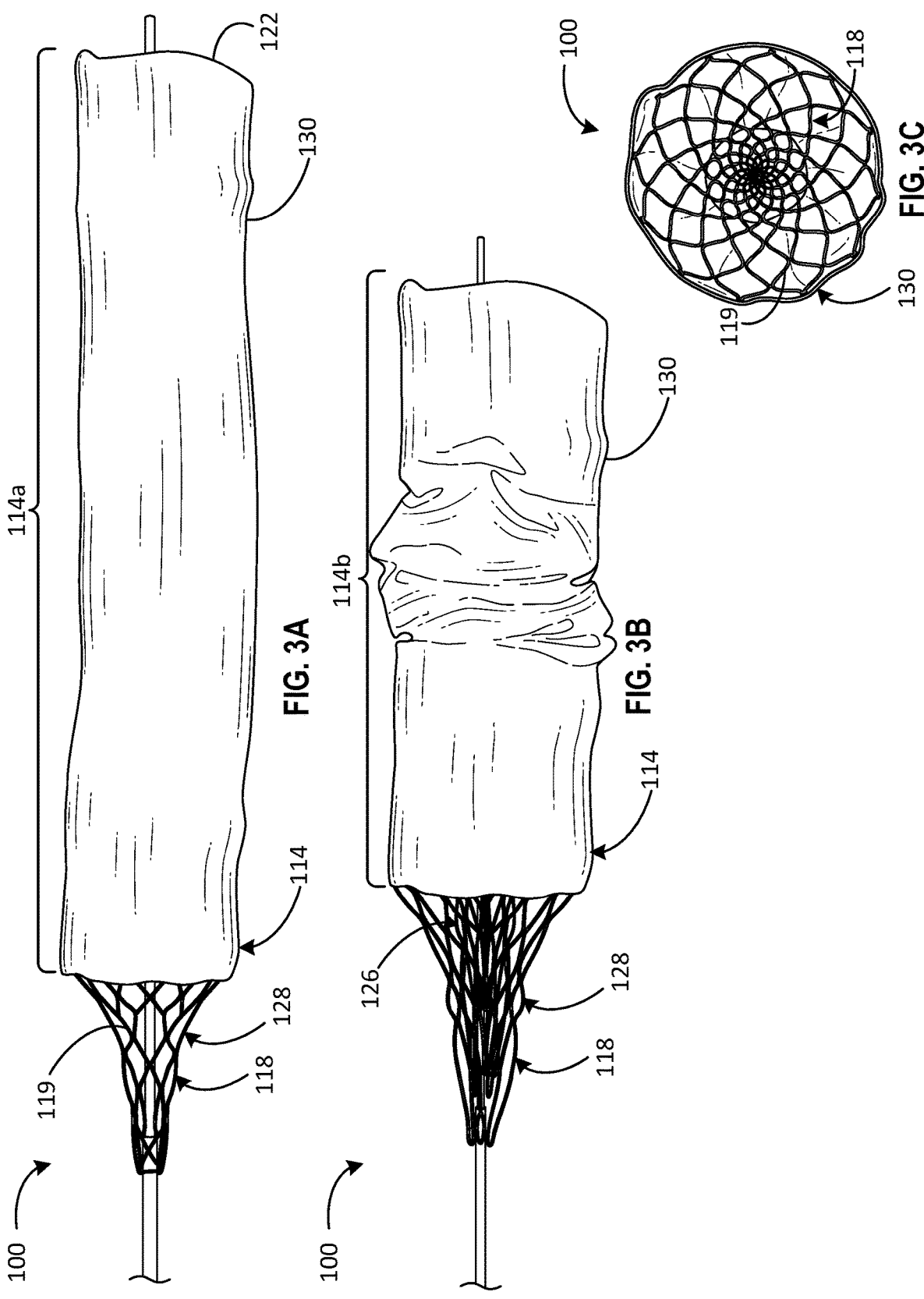
FIG. 3A is a partial side view of an endovascular assembly including a shunt in an elongated configuration.
FIG. 3B is a partial side view of the endovascular assembly of FIG. 3A, with the shunt in a shortened configuration.
FIG. 3C is a front view of the endovascular assembly of FIG. 3B.

FIG. 3A is a partial side view of an endovascular assembly 100 including a shunt 114 in an elongated configuration 114a. The endovascular assembly 100 is similar to the endovascular assembly 10 of FIGS. 1A to 2B in that the endovascular assembly also includes a shunt (shunt 114) including a frame (frame 118) and a liner (liner 130). Elements having like function are numbered alike. The structure and composition of the liner 130 may be substantially similar to the liner 30. The frame 118, while capable of radial collapse and expansion and longitudinal compression and elongation like frame 18, has a different structure than frame 18.

In particular, the frame 118 includes a pattern of struts 119. The struts 119 may be arranged in polygonal, curved, or complex or combined patterns. For example, the struts 119 may generally form diamond-shaped cells of the frame 118. The struts 119 of a cell may change in orientation and angle, allowing the cell to expand or contract. Generally, the struts 119 collectively may move to permit the frame 118 to collapse or expand radially. In some aspects, the struts 119 may move to permit the frame 118 to shorten or elongate longitudinally. In some embodiments, the frame 118 may include a material laser cut in a crisscross pattern, ultimately forming the struts 119. The material of the frame 118 may be similar to that described with reference to the frame 18.

In some embodiments, the entire frame 118 may be formed in a generally a cylindrical shape, with the struts 119 extending along the entire cylindrical shape. Thus, the overall dimensions of the cylindrical shape of the frame 118 itself may be changed, for example, one or both longitudinally or radially. The liner 130 may be secured to the frame 118 or about the frame 130 such that the liner 130 may move in response to the movement of the frame 118.

In some aspects, the frame 118 may be formed in two or more separate and spaced-apart sections, and the sections may individually be movable. For example, the individual sections may expand or collapse to cause the frame 118 to expand or collapse, and a relative movement of the sections toward each other may cause the frame 118 to be shortened, while a relative movement of the sections away from each other may cause the frame 118 to be elongated.

For example, the frame 118 may include a distal anchor 126 and a proximal anchor 128, and these anchors may constitute sections that may exhibit relative movement allowing a change between a shortened and an elongated configuration. In some embodiments, the anchors 126 and 128 themselves include patterns of the struts 119, and the frame may not include any struts 119 other than in the anchors 126 and 128.

FIG. 3B is a partial side view of the endovascular assembly 100 of FIG. 3A, with the shunt 114 in a shortened configuration 114b. FIG. 3C is a front view of the endovascular assembly 100 of FIG. 3B. In particular, in the shortened configuration 114b, the distal anchor 126 is withdrawn toward and into the proximal anchor 128, thus shortening the overall length of the shunt 114. In the elongated configuration 114a shown in FIG. 3A, the distal anchor 126 is spaced distally away from the proximal anchor 128 (within the shunt 114) toward a distal end 122 of the shunt 114, and not visible in FIG. 3A).

Figure 4A:
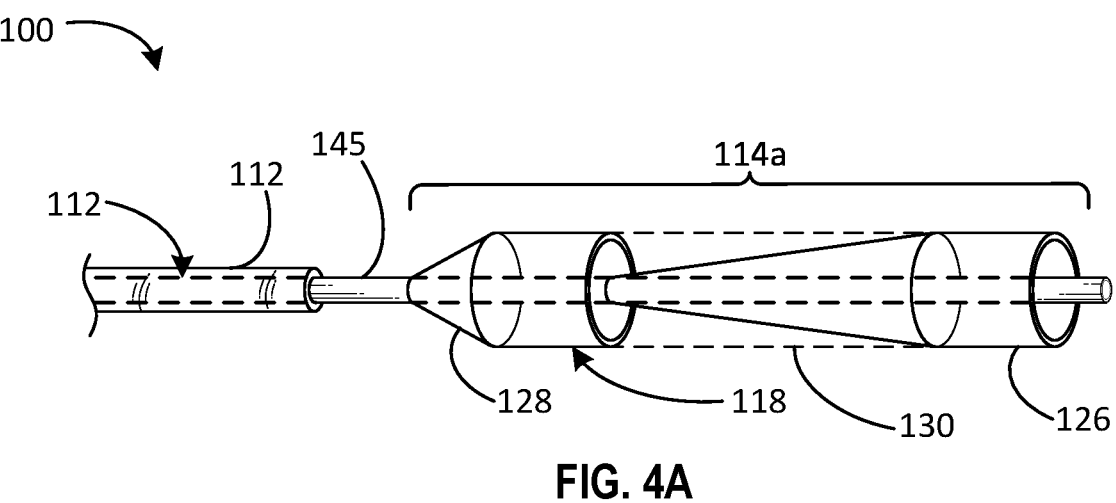
FIG. 4A is a partial side view of the endovascular assembly of FIG. 3A, showing a frame of the shunt in the elongated configuration.
Figure 4B:
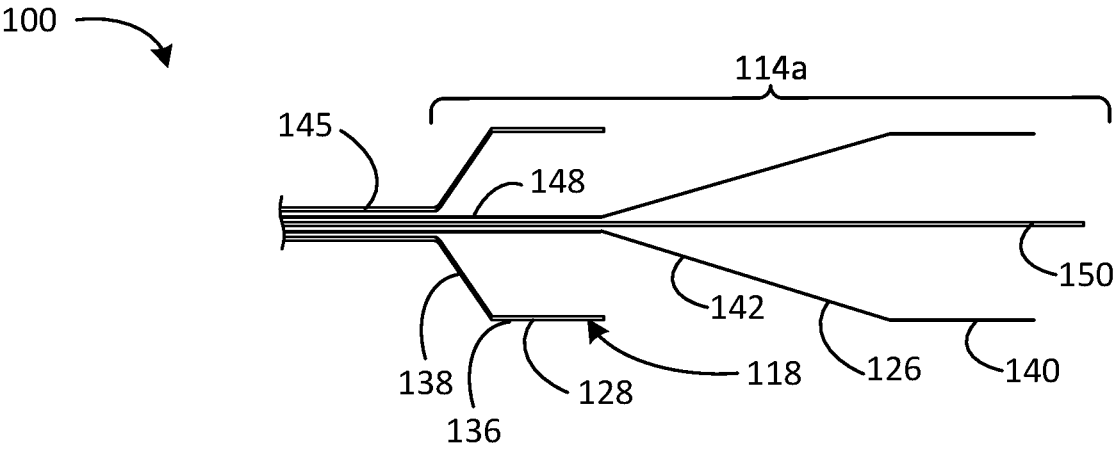
FIG. 4B is a partial cross-sectional view of the endovascular assembly of FIG. 4A, showing the frame of the shunt in the elongated configuration.
Figure 4C:
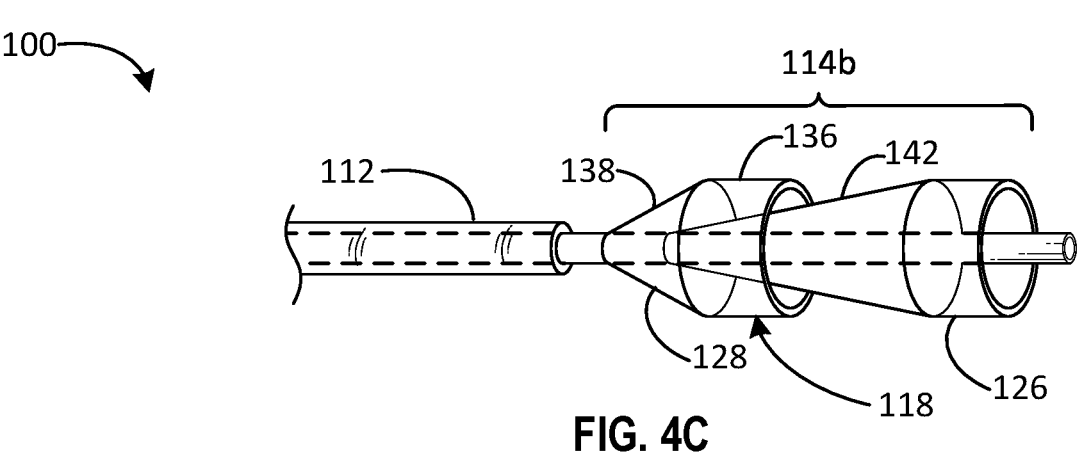
FIG. 4C is a partial side view of the endovascular assembly of FIG. 4A, showing the frame of the shunt in the shortened configuration.

The arrangement and relative movement of the distal anchor 126 and the proximal anchor 128, according to one embodiment, is shown in FIGS. 4A to 4C.

FIG. 4A is a partial side view of the endovascular assembly 100 of FIG. 3A, showing the frame 118 of the shunt 114 in the elongated configuration 114a. FIG. 4B is a partial cross-sectional view of the endovascular assembly 100 of FIG. 4A, showing the frame 118 of the shunt 114 in the elongated configuration 114a. The shunt 114 extends out from a catheter 112, which is similar to the catheter 12. The liner 130 is not shown in FIG. 4B. As seen in FIGS. 4A and 4B, in the elongated configuration 114a, the frame 118 is elongated because the anchors 126 and 128 are spaced apart. The liner 130 is relatively stretched into a cylindrical configuration in this configuration.

In some embodiments, the proximal anchor 128 includes a cylindrical anchor portion 136 coupled to a conical anchor portion 138. The cylindrical anchor portion 136 may be secured to an interior or exterior surface of the liner 130. The conical anchor portion 138 may extend proximally from the liner 130. For example, the liner 130 may only partially cover, or be absent from, the conical anchor portion 138 of the proximal anchor 128. Likewise, the distal anchor 126 may also include a cylindrical anchor portion 140 coupled to a conical anchor portion 142. The conical portion 142 may extend proximally within the shunt 114. The liner 130 may extend over and be coupled to the cylindrical anchor portion 140. For example, the liner 130 may extend over or along the conical anchor portion 138 without being attached to the conical anchor portion 138.

The liner 130 may be secured to the proximal and distal anchors 128 and 126. In some such embodiments, the liner 130 is substantially free between the proximal anchor and the distal anchor 128 and 126 to accommodate dimensional changes of the shunt 114. Thus, in aspects, one or both the distal anchor 126 and the proximal anchor 128 may attach to an internal surface of the liner 130. In other aspects, the proximal anchor 128 may attach to an external surface of the liner 130.

FIG. 4C is a partial side view of the endovascular assembly of FIG. 4A, showing the frame 118 of the shunt 114 in the shortened configuration 114b. As seen in FIG. 4C, in the shortened configuration 114b, the frame 118 is shortened because the anchors 126 and 128 are closer together longitudinally. The liner 130 is relatively shortened (as seen in corresponding FIG. 3B). Further, at least a portion of the distal anchor 126 may be received within a portion of the proximal anchor 128 in the shortened configuration 114b, as seen in FIGS. 3B and 4C.

A proximal end or portion of the distal anchor 126 may be received into an interior of the proximal anchor 128 when the shunt 114 is in the shortened configuration 114b, with the distal and proximal anchors 126 and 128 remaining at least partially coextensive. The coextensive anchors 126 and 128 may maintain the liner 130 when the shunt 114 is in the shortened configuration 114b, so that the liner 130 does not substantially radially collapse inward.

The length of the shunt 114 may be adjusted by relative motion between the proximal anchor 128 and the distal anchor 126. For example, the proximal anchor 128 may remain fixed, with a proximal movement of a wire bringing the distal anchor 126 towards the proximal anchor 128. Alternatively, the distal anchor 126 may remain fixed, such that a distal movement of the wire may bring the proximal anchor 128 towards the distal anchor 126.

One or both of the distal anchor 126 and the proximal anchor 128 may be formed as integral units. For example, the respective cylindrical anchor portions may continuously and integrally extend from the respective conical anchor portions.

The shunts 14 and 114 may be expandable to any suitable predetermined extent, for example, compared to a collapsed configuration. For example, the expanded maximum diameter may be in a ratio of at least 1.1, or at least 1.2, or at least 1.5, or at least 2, or at least 3, or at least 5, or at least 10, with respective to a collapsed diameter. Likewise, the shunts 14 and 114 may be lengthened to any predetermined length in the elongated configuration relative to the shortened configuration. For example, the elongated maximum length may be in a ratio of at least 1.1, or at least 1.2, or at least 1.5, or at least 2, or at least 3, or at least 5, or at least 10, with respective to a shortened length.

In some embodiments, the endovascular assembly 100 further includes a sheath 145 extending through a transport lumen 132 of the catheter 112. A wire may extend through the sheath 145. In some aspects, the sheath 145 is a first sheath, and the assembly 100 includes a second sheath 148. In some such aspects, one of the first and second sheaths 145 and 148 is telescoped within the other of the first and second sheaths 145 and 148. In some embodiments, a proximal wire may extend through the first sheath 145, while a distal wire extends through the second sheath 148.

In some embodiments, the distal anchor 126 is coupled to the distal wire. In some such embodiments, a proximal end of the conical anchor portion 142 is secured to the distal wire. In some embodiments, the proximal anchor 128 is coupled to a proximal wire. In some embodiments, a proximal end of the conical anchor portion 138 of the proximal anchor 128 is secured to the proximal wire.

In some embodiments, the assembly 100 may include proximal or distal wires, and the anchors may be secured to respective sheaths. For example, the proximal anchor 128 may be secured to the first sheath 145, and the distal anchor may be secured to the second sheath 148. Relative movement between the first and second sheaths 145 and 148 may be used to cause relative motion between the proximal and distal anchors 128 and 126, ultimately moving the shunt 114 between the elongated configuration 114a and the shortened configuration 114b. In some embodiments, the second sheath 148 may have a diameter of approximately 1.5 mm, and the first sheath 145 may have a diameter of approximately 2.0 mm.

The endovascular assembly 100 may include a wire 150, where the wire 150 is at least as long as the liner 130. The wire 150 may attach to the frame 118 and, in some aspects, the wire 150 may attach to or pass through one or both of the proximal and distal anchors 128 and 126.

In some embodiments, a maximum length of the shunt 114 may be approximately 20 cm. In some such embodiments, the distal anchor 126 may be approximately 15 cm long such that the distal anchor 126 may extend a majority of the length of the shunt 114. In some embodiments, the cylindrical anchor portion 138 of the proximal anchor 128 is approximately 4 cm, such that together the distal anchor 126 and the cylindrical portion 138 of the proximal anchor 128 span nearly the entire length of the liner 130 of the shunt 114. In the shortened configuration 114b, shown in FIG. 4C, the length of the shunt 114 may be approximately 10 cm.

Similar to the endovascular assembly 10, the endovascular assembly 100 also may carry the shunt 114 in a collapsed configuration within the transport lumen 132 of the catheter 112. Like shunt 14, the shunt 114 may move between the collapsed configuration and the expanded configuration in response to relative motion between the catheter 112 and the shunt 114.

Endovascular assemblies according to the present disclosure may include further components to facilitate navigation through vessels. For example, an endovascular assembly may further include an atraumatic tip, as described with reference to FIGS. 5A to 5D.

Figures 5A, 5B, 5C, 5D:
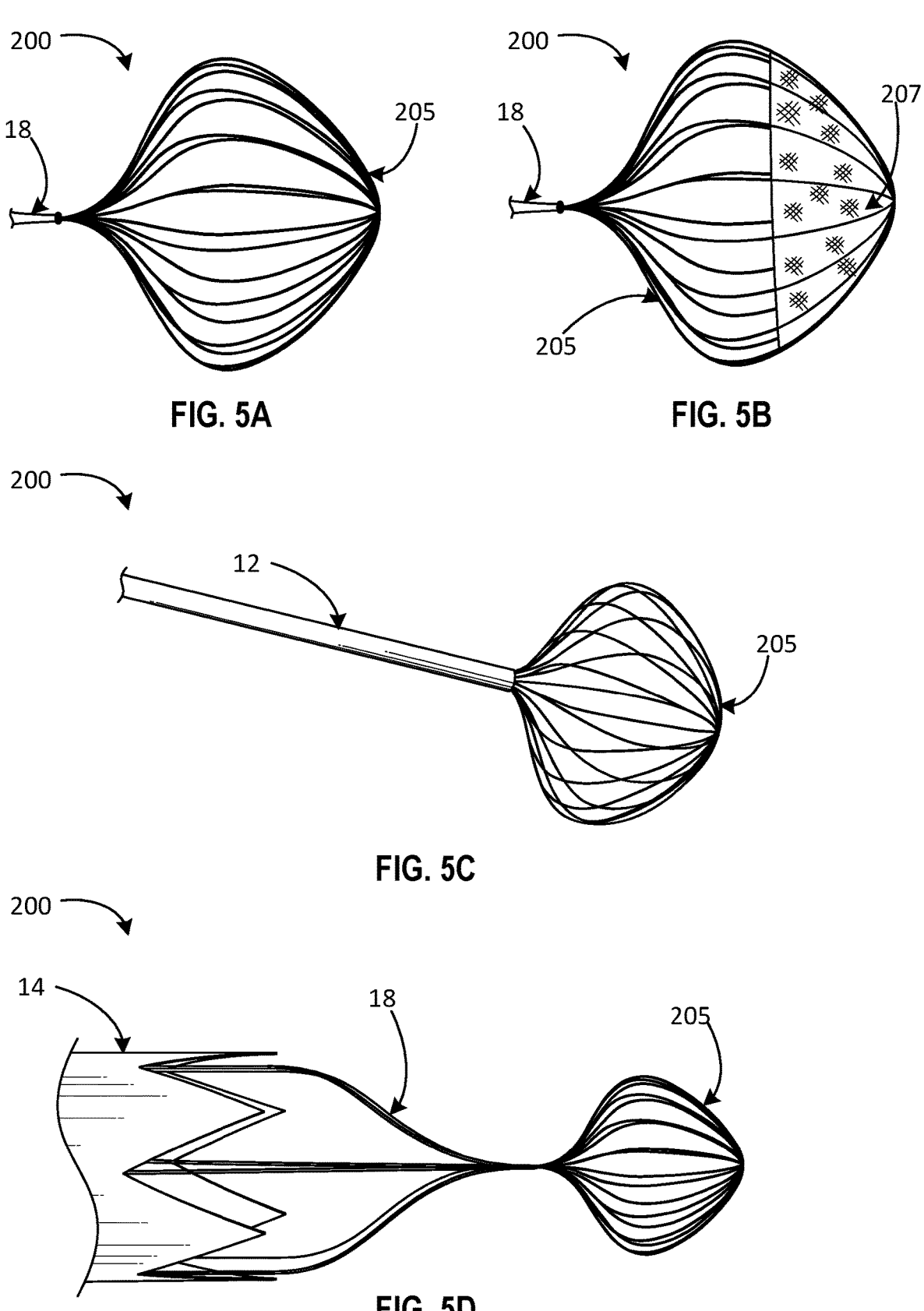
FIG. 5A is a partial side view of an endovascular assembly including an atraumatic tip.
FIG. 5B is a partial side view of the atraumatic tip, further including a liner.
FIG. 5C is a partial perspective view of the endovascular assembly of FIG. 5A with the shunt in a collapsed configuration, and the atraumatic tip protruding from the catheter.
FIG. 5D is a partial side view of the endovascular assembly of FIG. 5A with the shunt in an expanded configuration, and the atraumatic tip extending from the shunt.

FIG. 5A is a partial side view of an endovascular assembly 200 including an atraumatic tip 205. The endovascular assembly 200 may be substantially the same as either endovascular assembly 10 or endovascular 100, and further including the atraumatic tip 205. While the assembly 200 is described with reference to components of assembly 10, it will be understood that similar components of the assembly 100 may be used instead. In some embodiments, the atraumatic tip 205 is secured to a distal end of the frame 18. In some embodiments, the atraumatic tip 205 includes an atraumatic whisk. A form such as a whisk may be relatively easier to insert into an introducer sheath instead of an atraumatic tip formed as a portion of a relatively soft end or tip of a catheter.

In some embodiments, the atraumatic tip 205 has a shape that spreads the force associated with a catheter tip impact over a relatively large surface area. In some embodiments, the atraumatic tip 205 may filter or trap clots that may otherwise flow through the shunt 14. The atraumatic tip 205 may help to guide the catheter 12 through only relatively large pathways in a vessel. In some such embodiments, the atraumatic tip 205 may be retained in the catheter 12 in a compact or streamlined form during initial insertion of the catheter 12, and then allowed to expand to a more voluminous form upon emergence from the catheter 12. The expanded form of the atraumatic tip 205 may be used during travel within of the catheter 12 within the blood. The atraumatic tip 205 may remain expanded after the shunt 14 is deployed, for example, to function as a filter. In some such embodiments, the atraumatic tip 205 (for example, including the atraumatic whisk) may act as an inferior vena cava (IVC) filter.

FIG. 5B is a partial side view of an endovascular assembly 200, including an atraumatic tip 205, and further including a liner 207. In some embodiments, the liner 207 includes a porous mesh. The porous mesh may trap relatively small clots, tissue, or debris. In some embodiments, the liner 207 is formed of a material similar to that described with reference to the liner 30.

FIG. 5C is a partial perspective view of the endovascular assembly of FIG. 5A with the shunt in a collapsed configuration, and the atraumatic tip 205 protruding from the catheter 12. FIG. 5D is a partial side view of the endovascular assembly of FIG. 5A with the shunt 14 in an expanded configuration, and the atraumatic tip 205 extending from the shunt.

The atraumatic tip 205 may comprise several strands of a material, for example, a biocompatible polymer, metal, or an alloy. In some embodiments, the tip 205 includes nitinol wire. The material of the atraumatic tip 205 may be bent, machined, formed, or laser-cut to form a whisk.

While the catheter 12 is being inserted into the patient's vessel, the atraumatic tip 205 may be fully contained within the transport lumen of the catheter 12. Once the catheter 12 is inserted into the vessel, the catheter 12 may be partially retracted to expose the atraumatic tip 205.

In some embodiments, the catheter 12 is fitted with an introducer sleeve (not shown) that covers the tip of the catheter 12 during insertion. The introducer sleeve may have an internal diameter that is slightly larger than the external diameter of the catheter 12 such that the introducer sleeve remains external to the catheter 12 at all times. As the catheter 12 advances, the catheter 12 may slide through the introducer sleeve to expose the atraumatic tip 205 that was retained within the introducer sleeve during the initial insertion of the catheter 12 into the vessel. Once the catheter 12 has been inserted, the atraumatic tip 205 may protrude from the tip of the catheter 12 while the catheter 12 is being guided to the desired location within the blood vessel, as shown in FIG. 5C.

The catheter 12 with the protruding atraumatic tip 205 may be navigated through a patient's vasculature. The atraumatic tip 205 may prevent the catheter 12 from engaging a patient's vasculature because the atraumatic tip may have a greater surface area that the tip of the catheter 12. The atraumatic tip 205 may prevent the catheter 122 from entering into voids in a patient's vasculature.

After the catheter 12, attached to the atraumatic tip 205, is navigated to the desired location in a patient's vasculature, the shunt 14 may be deployed from the catheter 12. As shown in FIG. 5D, the atraumatic tip 205 may be distal to the shunt 14. In some embodiments, the atraumatic tip 205 may filter and break apart blood clots within a patient's vasculature. In some embodiments, the liner 207 may filter small blood clots that may otherwise pass through the whisk 205.

Endovascular assemblies according to the disclosure may be used to provide shunts within vessels of patients. Advantageously, shunts may always remain secured to a wire (or a sheath, or a catheter), thus allowing relatively rapid deployment and removal, and without requiring radio imaging or major surgery for placement of or removal of the shunt.

Figure 6:
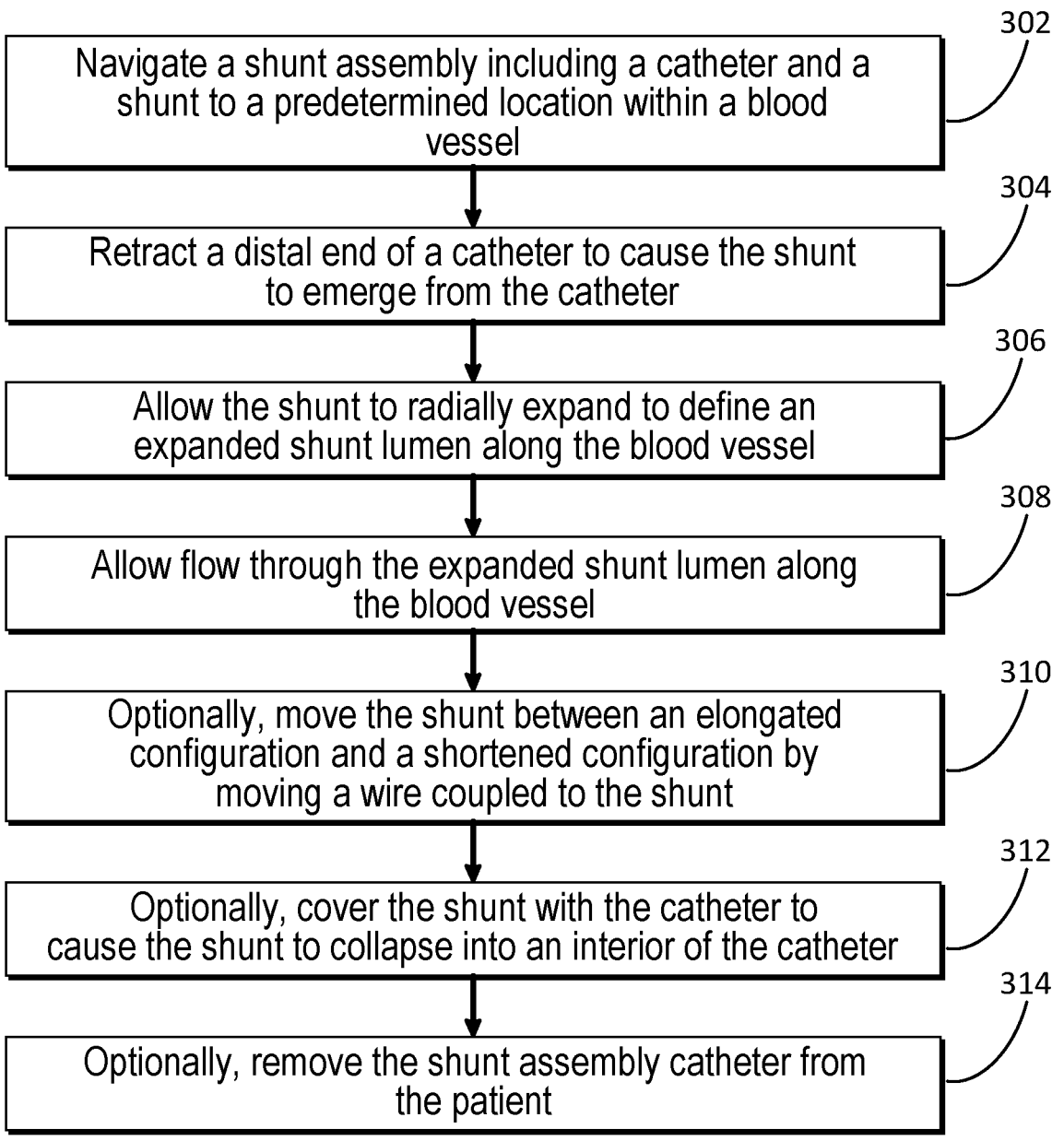
FIG. 6 is a flow diagram showing a method of shunting an endovascular vessel.

FIG. 6 is a flow diagram showing a method of shunting an endovascular vessel. The method of FIG. 6 may be practiced using any suitable endovascular assembly according to the present disclosure.

The method includes navigating an endovascular assembly or a shunt assembly to a predetermined location within the patient's vasculature, for example, into a blood vessel (302). The endovascular assembly or the shunt assembly includes a catheter and a shunt within the catheter. The shunt includes a frame and a liner. In some aspects, the location may be the site of a vascular injury.

The method may further include retracting a distal end of the catheter to cause the shunt to emerge from the catheter (304). For example, once the endovascular assembly is at the predetermined location, the distal end of the catheter may be retracted such that the shunt may emerge from the catheter. When the shunt begins to emerge from the catheter, the shunt may radially expand. The expanded shunt may define an expanded internal lumen of the shunt so that blood may pass through the shunt when it is expanded with a patient's vasculature.

The method may further include allowing the shunt to radially expand to define an expanded shunt lumen along the blood vessel (306). In some embodiments, an outer surface of the liner is configured to contact an inner surface of the blood vessel. In some such embodiments, the contact between the inner surface of the blood vessel and the outer surface of the liner forms a seal reducing or preventing transverse flow out of the blood vessel. Thus, the shunt may be effective to reduce or prevent hemorrhaging.

In some embodiments, the shunt may be partially deployed, for example, less than completely expanded. In some embodiments, partial or complete deployment of the shunt may be used to reduce or block blood flow in a vessel. For example, blood supply to a predetermined vessel, tissue, organ, or region of the body may be restricted by blocked by partially or completely deploying the shunt.

In some embodiments, the position of the shunt may require adjusting after the shunt has been deployed. To advance the shunt forward, the endovascular assembly may be pushed forward from a control point outside of a patient's body. To reverse the shunt, the endovascular assembly may be pulled back from a control point outside of a patient's body.

The method may further include allowing blood flow through the expanded shunt lumen along the blood vessel (308).

The method may further optionally include moving the shunt between an elongated configuration and a shortened configuration by moving a wire coupled to the shunt (310). In some embodiments, the length of the shunt may require adjusting after the shunt has been deployed within a patient's vasculature. The length of the shunt may be shortened by moving a wire coupled to the shunt. To lengthen the shunt after it has been shortened, the wire may be moved in the opposite direction to expand the shunt's length. The method may further optionally include covering the shunt with the catheter to cause the shunt to collapse into an interior of the catheter (312).

While the shunt is deployed within a patient's vasculature, the shunt may prevent rapid blood loss so that a clinician may repair a patient's vascular injury. When the surgical repair is complete, the shunt may be returned to the interior lumen of the catheter. To return the shunt to the catheter, the catheter may be advanced over the shunt to collapse the shunt diameter so that it may fit within the catheter. Once the shunt is fully contained within the catheter, the endovascular assembly may be removed. The method may further optionally include removing the shunt assembly catheter from the patient (314).

In some embodiments the endovascular assembly or the shunt assembly includes an atraumatic tip, for example, an atraumatic whisk. In some such embodiments, the atraumatic whisk may be expandable. The atraumatic whisk may initially remain constrained within the catheter, and subsequently allowed to expand upon emerging from the catheter. For example, only the atraumatic tip may initially emerge from the catheter and expand, with the shunt remaining within the catheter. The atraumatic tip may thus protect inner surfaces of blood vessels, or other surfaces or tissue within the body, from an end of the catheter or an end of the shunt. In some such embodiments, the atraumatic whisk may act as an inferior vena cava (IVC) filter.

While assemblies and methods have been described in the present disclosure with reference to the endovascular system and blood vessels, assemblies and methods according to the present disclosure may be used to provide a shunt within any target lumen, or within a lumen of any elongated object, such as a pipe.

As used herein, the term "approximately" means plus or minus 10% of the numerical value of the number with which it is being used.

While the disclosure has been described with reference to a number of aspects, it will be understood by those skilled in the art that the disclosure is not limited to such disclosed aspects. Rather, the disclosed aspects can be modified to incorporate any number of variations, alterations, substitutions, or equivalent arrangements not described herein, but which are within the scope of the disclosure.

ASPECTS

1. An endovascular assembly including:
    a catheter defining a transport lumen extending from a proximal end of the catheter to a distal end of the catheter;
    a shunt including a frame and a liner secured about the frame; and
    a wire extending through the transport lumen of the catheter and coupled to the shunt, where the shunt is configured to move, in response to a relative movement between the catheter and the shunt, between (1) a collapsed configuration within the transport lumen of the catheter and (2) an expanded configuration defining an expanded shunt lumen outside the transport lumen.

2. The endovascular assembly of aspect 1, where the frame is biased to expand radially, to cause the shunt to expand from the collapsed configuration to the expanded configuration when the shunt emerges from the distal end of the catheter.

3. The endovascular assembly of aspects 1 or 2, where the frame is configured to collapse when a proximal end of the shunt is withdrawn proximally into the distal end of the catheter.

4. The endovascular assembly of any of aspects 1 to 3, where the frame is configured to move in a direction along the shunt between an elongated configuration and a shortened configuration in response to a relative movement between the wire and the catheter.

5. The endovascular assembly of aspect 4, where the radial dimension of the shunt is substantially unchanged in the elongated configuration and the shortened configuration.

6. The endovascular assembly of aspects 4 or 5, where the wire is coupled to a distal end of the frame.

7. The endovascular assembly of aspects 4 or 5, where the wire is coupled to a proximal end of the frame.

8. The endovascular assembly of any of aspects 4 to 7, where the wire is a proximal wire coupled to a proximal end of the frame, where the endovascular assembly further includes a distal wire coupled to a distal end of the frame, and where the frame is configured to change in length in response to a relative movement between the proximal wire and the distal wire.

9. The endovascular assembly of any of aspects 4 to 8, further including a sheath extending through the transport lumen of the catheter, where the wire extends through the sheath.

10. The endovascular assembly of aspect 9, where the sheath is a first sheath through which the proximal wire extends, where the endovascular assembly further includes a second sheath through which the distal wire extends.

11. The endovascular assembly of aspect 10, where one of the first sheath and the second sheath is telescoped within the other of the first sheath and the second sheath.

12. The endovascular assembly of any of aspects 1 to 11, where the frame includes nitinol.

13. The endovascular assembly of any of aspects 1 to 12, where the liner includes a fabric or a film.

14. The endovascular assembly of aspect 13, where the liner includes a flexible polymer.

15. The endovascular assembly of aspect 14, where the liner includes polytetrafluoroethylene (PTFE).

16. The endovascular assembly of any of aspects 1 to 15, where the liner includes a semi-permeable material.

17. The endovascular assembly of any of aspects 1 to 16, where the frame includes a proximal anchor and a distal anchor, and where the liner is secured to the proximal and distal anchors.

18. The endovascular assembly of aspect 17, where the liner is substantially free between the proximal anchor and the distal anchor.

19. The endovascular assembly of aspects 17 or 18, where the proximal anchor is coupled to the proximal wire.

20. The endovascular assembly of any of aspects 17 to 19, where the proximal anchor includes a cylindrical anchor portion coupled to a conical anchor portion, where the cylindrical anchor portion is secured to an interior surface of the liner, where the conical anchor portion extends proximally from the liner, and where a proximal end of the conical anchor portion is secured to the proximal wire.

21. The endovascular assembly of any of aspects 17 to 20, where the distal anchor is secured to the distal wire.

22. The endovascular assembly of aspect 21, where the distal anchor includes a conical portion extending proximally within the shunt, and where a proximal end of the conical anchor is secured to the distal wire.

23. The endovascular assembly of any of aspects 17 to 22, where the proximal anchor is secured to the first sheath.

24. The endovascular assembly of any of aspects 17 to 23, where the distal anchor is secured to the second sheath.

25. The endovascular assembly of any of aspects 1 to 24, further including an atraumatic tip, where the atraumatic tip is secured to the distal end of the frame.

26. The endovascular assembly of aspect 25, where the atraumatic tip includes an atraumatic whisk.

27. The endovascular assembly of aspect 26, where the whisk is lined with a porous mesh.

28. An endovascular shunt including:
   a frame; and
   a liner secured about the frame,
   where the shunt is configured to move between (i) a collapsed configuration and (ii) an expanded configuration defining an expanded shunt lumen.

29. The endovascular shunt of aspect 28, where the frame is biased to expand radially, to cause the shunt to expand from the collapsed configuration to the expanded configuration.

30. The endovascular shunt of aspects 28 or 29, further including a wire coupled to the frame, where the frame is configured to move between an elongated configuration and a shortened configuration in a direction along the shunt in response to a movement of the wire.

31. A method of shunting a blood vessel including:
   navigating a shunt assembly including a catheter and a shunt within the catheter to a predetermined location within the blood vessel, where the shunt includes a frame and a liner;
   retracting a distal end of the catheter to cause the shunt to emerge from the catheter;
   allowing the shunt to radially expand to define an expanded shunt lumen along the blood vessel; and
   allowing flow through the expanded shunt lumen along the blood vessel.

32. The method of aspect 31, where an outer surface of the liner is configured to contact an inner surface of the blood vessel.

33. The method of aspect 32, where the contact between the inner surface of the blood vessel and the outer surface of the liner forms a seal reducing or preventing transverse flow out of the blood vessel.

34. The method of any of aspects 31 to 33, where the shunt is effective to reduce or prevent hemorrhaging.

35. The method of any of aspects 31 to 34, further including:
   covering the shunt with the catheter to cause the shunt to collapse into an interior of the catheter; and
   removing the shunt assembly catheter from the patient.

36. The method of any of aspects 31 to 35, further including moving the shunt between an elongated configuration and a shortened configuration by moving a wire coupled to the shunt.

37. An assembly including:
   a catheter defining a transport lumen extending from a proximal end of the catheter to a distal end of the catheter;
   a shunt including a frame and a liner secured about the frame; and
   a wire extending through the transport lumen of the catheter and coupled to the shunt,
   where the shunt is configured to move or transition, in response to a relative movement between the catheter and the shunt, between (1) a collapsed configuration within the transport lumen of the catheter and (2) an expanded configuration defining an expanded shunt lumen outside the transport lumen.

38. A shunt including:
   a frame; and
   a liner secured about the frame,
   where the shunt is configured to move or transition between (i) a collapsed configuration and (ii) an expanded configuration defining an expanded shunt lumen.

39. A method of shunting a target lumen including:
   navigating an assembly including a catheter and a shunt within the catheter to a predetermined location within the target lumen, where the shunt includes a frame and a liner;
   retracting a distal end of the catheter relative to the shunt or to connecting wires coupled to the assembly to cause the shunt to emerge from the catheter;
   allowing the shunt to radially expand to define an expanded shunt lumen along the target lumen; and
   allowing flow through the expanded shunt lumen along the target lumen.

What is claimed is:

1. An endovascular assembly comprising:
   a catheter defining a transport lumen extending from a proximal end of the catheter to a distal end of the catheter; and
   a shunt comprising:
      a proximal frame and a proximal wire coupled to and extending from the proximal frame;
      a distal frame and a distal wire coupled to and extending from the proximal frame; and
      a liner coupled to and extending between both the proximal frame and the distal frame, the proximal frame and the distal frame being formed separately and coupled together directly only via the liner,
   wherein the proximal wire is configured to extend proximally from the proximal frame through the transport lumen of the catheter, and the distal wire is configured to extend proximally from the distal frame,
   wherein the shunt is configured to move between (1) a collapsed configuration in which the shunt is constrained within the transport lumen of the catheter and has a first diameter, and (2) an expanded configuration in which the shunt is exposed from the transport lumen and has a second diameter greater than the first diameter, and
   wherein the shunt is configured to move between (1) an elongated configuration in which the distal frame is spaced from the proximal frame by a first distance and (2) a shortened configuration in which the distal frame is spaced from the proximal frame by a second distance less than the first distance.

2. The endovascular assembly of claim 1, wherein the proximal frame and the distal frame are biased to expand radially, to cause the shunt to expand from the collapsed configuration to the expanded configuration when the shunt emerges from the distal end of the catheter.

3. The endovascular assembly of claim 1, wherein the proximal frame and the distal frame are configured to collapse when a proximal end of the shunt is withdrawn proximally into the distal end of the catheter.

4. The endovascular assembly of claim 1, wherein the distal frame is configured to move in a direction along the shunt between the elongated configuration and the shortened configuration in response to a relative movement between the distal wire and the catheter.

5. The endovascular assembly of claim 4, wherein a radial dimension of the shunt is unchanged in the elongated configuration and the shortened configuration.

6. The endovascular assembly of claim 4, wherein the distal wire is coupled to the proximal end of the distal frame.

7. The endovascular assembly of claim 4, further comprising a sheath extending through the transport lumen of the catheter, wherein the distal wire extends through the sheath.

8. The endovascular assembly of claim 1, wherein the proximal frame and the distal frame comprise nitinol.

9. The endovascular assembly of claim 1, wherein the liner comprises a fabric or a film.

10. The endovascular assembly of claim 1, wherein the liner comprises polytetrafluoroethylene (PTFE).

11. The endovascular assembly of claim 1, wherein the proximal frame comprises a proximal anchor and the distal frame comprises a distal anchor, and wherein the liner is secured to the proximal and distal anchors.

12. The endovascular assembly of claim 11, wherein the proximal anchor comprises a cylindrical anchor portion coupled to a conical anchor portion, wherein the cylindrical anchor portion is secured to an interior surface of the liner, wherein the conical anchor portion extends proximally from the liner, and wherein a proximal end of the conical anchor portion is secured to the proximal wire.

13. The endovascular assembly of claim 11, wherein the distal anchor comprises a conical portion extending proximally within the shunt, and wherein a proximal end of the conical portion is secured to the distal wire.

14. The endovascular assembly of claim 11, wherein a portion of the distal anchor is configured to be received within a portion of the proximal anchor when the shunt is transitioned to the shortened configuration.

15. The endovascular assembly of claim 14, wherein the portion of the distal anchor is a first sheath extending proximally away from the distal anchor, wherein the portion of the proximal anchor is a second sheath extending proximally away from the proximal anchor, the second sheath having a diameter greater than a diameter of the first sheath such that the first sheath is configured to be received within the second sheath.

16. The endovascular assembly of claim 1, further comprising an atraumatic tip, wherein the atraumatic tip is secured to a distal end of the distal frame, wherein the atraumatic tip is configured to be transitioned from a collapsed configuration to an expanded configuration when the atraumatic tip is deployed from the catheter.

17. The endovascular assembly of claim 16, wherein the atraumatic tip comprises an atraumatic whisk, wherein the atraumatic whisk further comprises a rounded distal end portion configured to guide the catheter through a vessel of a patient, wherein the rounded distal end portion is at least partially covered by a porous mesh.

18. The endovascular assembly of claim 1, wherein the shunt is configured to be deployed from the catheter without the aid of a guidewire.

19. The endovascular assembly of claim 1, wherein a proximal end of the distal frame is configured to be proximal to a proximal end of the liner in the shortened configuration.

20. The endovascular assembly of claim 1, wherein the liner is configured to span a gap across the first distance between the distal frame and the proximal frame when the shunt is in the elongated configuration.

21. An endovascular shunt comprising:

a frame including:

a proximal anchor; and a distal anchor movable relative to and nestable with the proximal anchor; and a liner secured about the proximal and distal anchors, wherein the shunt is configured to move (i) radially between a collapsed configuration and an expanded configuration and (ii) axially between an elongated configuration in which the proximal anchor is spaced a first distance from the distal anchor, and a shortened configuration in which the proximal anchor is spaced a second distance from the distal anchor, the second distance being less than the first distance.

22. The endovascular shunt of claim 21, wherein the frame is biased to expand radially, to cause the shunt to expand from the collapsed configuration to the expanded configuration.

23. The endovascular shunt of claim 21, wherein the frame includes a proximal frame portion including the proximal anchor, and a distal frame portion including the distal anchor, the distal frame portion being separate from the proximal frame portion.

24. The endovascular shunt of claim 23, wherein the liner includes a proximal end coupled to the proximal frame portion and a distal end coupled to the distal frame portion.

25. The endovascular shunt of claim 21, wherein the distal anchor is configured to be nested within the proximal anchor.

26. The endovascular shunt of claim 21, wherein the distal anchor is to be positioned at least partially within the proximal anchor in the shortened configuration.

27. The endovascular shunt of claim 21, wherein a radial dimension of the shunt is unchanged between the elongated configuration and the shortened configuration.

28. An endovascular assembly comprising:

a catheter defining a transport lumen extending therethrough; and a shunt comprising:

a distal frame and a distal elongate member coupled to and extending from the distal frame, and configured to extend proximally from the distal frame and through the transport lumen of the catheter and be manipulated to cause movement of the distal frame relative to the catheter and the proximal frame;

a proximal frame and a proximal elongate member coupled to and extending from the proximal frame, and configured to extend proximally from the proximal frame and through the transport lumen of the catheter and be manipulated to cause movement of the proximal frame relative to the catheter and the distal frame; and a liner secured about the distal frame and the proximal frame, wherein the proximal frame and the distal frame are coupled together directly only via the liner, wherein the shunt is configured to move between an elongated configuration in which the distal frame is axially offset from the proximal frame by a first distance and a shortened configuration in which the distal frame is axially offset from the proximal frame by a second distance less than the first distance, and wherein at least a portion of the liner is configured to extend axially across and circumferentially around an axial gap defined between the proximal frame and the distal frame when the shunt is in the elongated configuration.

29. The endovascular assembly of claim 28, wherein the shunt is configured to move, in response to a relative movement between the catheter and the shunt, between (1) a collapsed configuration within the transport lumen and (2) an expanded configuration defining an expanded shunt lumen outside the transport lumen.

30. The endovascular assembly of claim 28, wherein the proximal frame comprises a proximal anchor adjacent to a proximal end of the proximal frame and the distal frame comprises a distal anchor adjacent to a distal end of the distal frame, and wherein the proximal elongate member is secured to the proximal anchor and the distal elongate member is secured to the distal anchor.

31. The endovascular assembly of claim 30, wherein the proximal anchor comprises a cylindrical anchor portion coupled to a conical anchor portion, and wherein a proximal end of the conical anchor portion is secured to the proximal elongate member.

32. The endovascular assembly of claim 30, wherein the distal anchor comprises a conical portion extending proximally within the shunt, and wherein a proximal end of the conical portion is secured to the distal elongate member.

33. The endovascular assembly of claim 28, wherein a radial dimension of the shunt is substantially unchanged in the elongated configuration and the shortened configuration.

34. The endovascular assembly of claim 28, wherein the proximal elongate member is a wire or a sheath, and the distal elongate member is a wire or a sheath.

* * * * *